United States Patent [19]

Buglino et al.

[11] Patent Number: 6,011,194
[45] Date of Patent: Jan. 4, 2000

[54] WOUND DRESSING

[75] Inventors: Donald E. Buglino, Butler; Barry Constantine, Island Heights; Joanne C. Hudak, Belle Mead; Marjory A. Kadash, Skillman, all of N.J.

[73] Assignee: Bristol-Myers Squibb Company, New York, N.Y.

[21] Appl. No.: 09/126,892

[22] Filed: Jul. 31, 1998

Related U.S. Application Data

[60] Provisional application No. 60/054,401, Jul. 31, 1997.

[51] Int. Cl.⁷ .................................................. A61F 15/00
[52] U.S. Cl. ............................................. 602/41; 428/326
[58] Field of Search .................................. 602/41, 56, 49; 424/445, 374; 428/326

[56] References Cited

U.S. PATENT DOCUMENTS

| | | | |
|---|---|---|---|
| 2,379,657 | 7/1945 | Ryberg | 604/307 |
| 4,393,080 | 7/1983 | Pawelchak et al. | 428/355 |
| 4,909,243 | 3/1990 | Frank et al. | 128/156 |
| 5,056,510 | 10/1991 | Gilman | 128/155 |
| 5,106,362 | 4/1992 | Gilman | 602/47 |
| 5,250,043 | 10/1993 | Castellana et al. | 604/336 |
| 5,429,591 | 7/1995 | Yamamoto et al. | 602/54 |
| 5,603,946 | 2/1997 | Constantine | 424/445 |

*Primary Examiner*—John G. Weiss
*Assistant Examiner*—Kelvin Hart
*Attorney, Agent, or Firm*—John M. Kilcoyne; Theodore R. Furman, Jr.

[57] ABSTRACT

An improved wound dressing is provided according to the present invention. In a preferred embodiment, the dressing comprises an absorbent layer including one or more absorbent and/or superabsorbent materials; a porous, non-stick layer or film larger in size than said absorbent layer and overlying, a wound-facing surface of the absorbent layer such that a portion of the non-stick layer extends beyond the length and width of the absorbent layer; a protective cover layer, which protective cover layer is larger in size than the absorbent layer but generally no greater in size than the non-stick layer; and a cohesive layer of an adhesive material generally being substantially the size and shape of the protective cover layer which is adhered to its non-wound-facing surface and having the absorbent layer and the extending portion of the non-stick layer adhered to its wound facing surface, whereby a substantially non-adherent dressing is provided.

4 Claims, 2 Drawing Sheets

WOUND DRESSING

This application claims the benefit of U.S. Provisional application No. 60/054,401 filed Jul. 31, 1997.

FIELD OF THE INVENTION

The present invention relates to a wound dressing that is useful for the treatment of wounds.

BACKGROUND OF THE INVENTION

In connection with the care and treatment of wounds, the term "wound" is meant to include burns, pressure sores, punctures, ulcers and the like. For a long time, one critical aspect of wound care has been the consideration of the requirements of the epithelium, i. e., that area of new cell growth directly peripheral to the wound which is formed during the healing process, so that healing is facilitated.

Since it has been recognized that healing of the wound occurs in one sense as the epithelium migrates by growth from the periphery inward, care has been taken not to damage unnecessarily or to irritate this new area of growth or existing, compromised periwound tissue. With many dressings, problems can occur during dressing changes. This is particularly true where the dressing adheres to the epithelium or where granulation tissue and new cell growth become intertwined within the matrix of a dressing. In these instances, there is a risk that removal of the dressing will damage the sensitive tissue and new growth on the periphery of the wound thereby causing a regression in the progress of wound healing.

Another consideration in wound care is the frequency of dressing changes. The time frame for the changing of dressings depends on many concerns and therefore opinions as to how often dressings should be changed vary drastically.

Still, another important consideration in wound care is the needs of the surrounding unwounded skin. The unwounded skin beyond the epithelium is usually in contact with some portion of the wound dressing system which maintains the dressing positioned on the wound. For example, the surrounding skin may be covered for extended periods with a wrap and/or adhesive to hold the dressing in place. Many such dressings can irritate this surrounding skin and compound problems to the patient. This is especially true in the area of leg ulcers wherein the surrounding skin can easily become sensitized by strong medicaments and is often plagued with flaking, scaling and eczema.

One type of treatment presently used, in particular for leg ulcers, comprises the application of gauze to the ulcer and the utilization of a compression wrap to secure the gauze to the ulcer. Since the gauze quickly becomes saturated, frequent changes are necessary and damage to the epithelium and surrounding skin may occur. Moreover, if the gauze is left on for too long a period, the exudate can begin to overly hydrate and macerate the patient's surrounding skin.

A second type of treatment, also used in particular for leg ulcers, is the Unna's Boot (commercially available from Biersdorf, Inc.) which comprises a zinc paste-containing bandage wrapped around a patient's leg from above the toes to below the knee. Other Unna's Boot/zinc impregnated treatments are available from Miles and Graham Field. These dressings are typically left in place for a week at a time and absorbent pads must be applied to the outside of the dressings in the area of the ulcer to absorb excess exudate. Seepage of exudate throughout the wrap is common, and damage to the skin and epithelium is inevitable.

Another type of wound dressing is disclosed in U.S. Pat. No. 5,106,362 to Gilman. This dressing is provided with a base sheet for contacting the skin of a patient. The base sheet has an opening for placement over the wound. The dressing has a vent for providing controlled leakage of fluid along a path from the wound through the opening of the base sheet. The vent is designed to provide control over wound leakage along a "tortuous path" from the wound through the opening of the base sheet.

A modification of the dressing of U.S. Pat. No. 5,106,362 is disclosed in U.S. Pat. No. 5,056,510, also to Gilman. The '510 patent discloses a vented dressing where the fabric reservoir for wound exudate is contained within a chamber. The walls of the chamber are intended to provide a barrier to bacterial and other contaminants. The walls of the chamber are also intended to be air permeable so as to permit egress of air from the voids of the fabric reservoir. These Gilman dressings do not especially address the problems of the epithelium and the surrounding skin.

U.S. Pat. No. 4,909,243 to Frank et al., which is owned by the assignee of the present invention, discloses a two piece wound dressing comprising a baseplate having an adhesive surface for contacting surrounding skin. The baseplate has an aperture extending completely through the baseplate and around the wound over which a wound pad of a desired wound dressing material can be placed. The purpose of the aperture is to permit visualization of the wound.

U.S. Pat. No. 4,485,809 to Dellas relates to a film window dressing. There is a central region or window defined by perforation lines which is applied to a patient. The perimeter or window frame which is used to permit easier handling is then removed.

It is apparent that, considering the various types of wounds, the numerous dressings that are available, and the various stages of healing, there is still a tremendous need for a dressing that functions better than the current dressings, especially with respect to preventing damage to surrounding skin, tissue and new cell growth. In particular, a wound dressing system which protects the epithelium and surrounding non-wounded skin, which wicks away moisture from the wound area, and which does not purposely adhere to the wound or the surrounding area would be a useful addition to the wound care art. A dressing for patients with fragile skin surrounding a wound would be especially beneficial.

SUMMARY OF THE PRESENT INVENTION

It has become clear in the art that the current dressings described above may be insufficient for many wounds. For instance, gauze applied to a leg ulcer and secured in place by a compression wrap requires too many dressing changes. The two piece dressing described above in Frank et al. (U.S. Pat. No. 4,909,243) has also proved to be unsatisfactory in practice. In particular, the baseplate was unwieldy. The market place is looking for an absorbent dressing that is easy to manage, does not adhere to skin surrounding a wound and does not require frequent changing. The instant invention provides such a dressing.

In accordance with the present invention, then, there is provided an improved wound dressing. In a preferred embodiment, the dressing comprises an absorbent layer including one or more absorbent and/or superabsorbent materials; a porous, non-stick layer or film larger in size than said absorbent layer and overlying a wound-facing surface of the absorbent layer such that a portion of the non-stick layer extends beyond the length and width of the absorbent layer; a protective cover layer, which protective cover layer is larger in size than the absorbent layer but generally no greater in size than the non-stick layer; and a cohesive layer of an adhesive material generally being substantially the size and shape of the protective cover layer which is adhered to its non-wound-facing surface and having the absorbent layer and the extending portion of the non-stick layer adhered to its wound facing surface, whereby a substantially non-adherent dressing is provided.

DETAILED DESCRIPTION OF THE INVENTION

Figure 1:
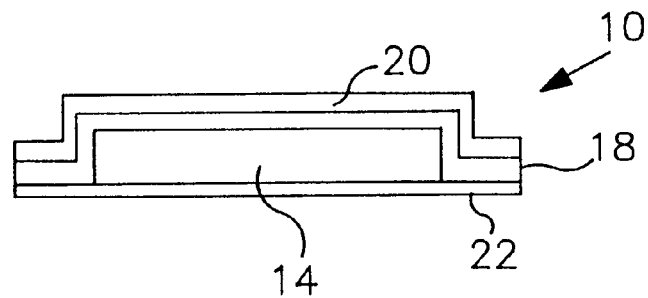
FIG. 1 is a cross-sectional view of one embodiment of the present invention.
Figure 5:
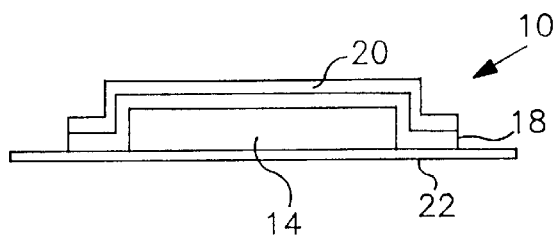
FIG. 5 is a cross-sectional view of a second embodiment of the present invention.

Referring to FIGS. 1 and 5, two embodiments of the wound dressing 10 of the present invention are shown to have an absorbent layer including an absorbing means or wound pad 14 designed to fit over the wound (not shown). The wound dressing 10 also comprises a cohesive layer 18, a protective cover backing film 20 which overlies the cohesive layer 18, and a porous, non-stick layer or film 22.

The cohesive layer 18 comprises any acrylic adhesives or other pressure sensitive adhesives suitable for use in wound dressings. The cohesive layer 18 may comprise an adhesive mass of adhesive material. Alternatively, fluid interactive adhesives known in the art for the treatment of wounds which emit exudate, can be used and they typically comprise hydrocolloids dispersed in a polymer matrix. Also, the adhesive material may be one capable of adhering to moist surfaces. Adhesive compositions known in the art for use in ostomy skin barriers and male incontinence applications can be well-suited for use in the present invention. However, no particular characteristic of the adhesive is necessary. It simply must hold the other layers together.

Some adhesives which have been used in wound dressings include those described in U.S. Pat. No. 3,339,545 to Chen. Chen discloses an adhesive comprising a blend of one or more water soluble or water swellable hydrocolloids and a viscous substance such as polyisobutylene. A film of water insoluble material, corresponding to the backing film in the instant case, is affixed to one surface of the adhesive. The article is commercially available as Stomahesive™ and Durahesive from ConvaTec.

Doyle et al., in U.S. Pat. No. 4,551,990, disclose a pressure sensitive adhesive suitable for medical purposes comprising 5 to 30 percent by weight of one or more polyisobutylenes or a blend of one or more polyisobutylenes and butyl rubber, 3 to 20 percent by weight of one or more styrene radial or block type copolymers, 8 to 40 percent by weight of mineral oil, 15 to 65 percent by weight of one or more water soluble hydrocolloid gums, up to 15 percent by weight of one or more water swellable cohesive strengthening agents provided that the hydrocolloid gums and strengthening agents together are present in an amount of between about 15 and 65 percent by weight, and 7.5 to 15 percent by weight of a tackifier.

Pawelchak et al., in U.S. Pat. No. 4,393,080, disclose an adhesive composition comprising 30 to 70 percent by weight of a pressure sensitive viscous adhesive material and an optional thermoplastic elastomer. The pressure sensitive material is selected from natural rubber, silicone rubber, acrylonitrile rubber, polyurethane rubber and polyisobutylenes. The elastomer can be medium molecular weight polyisobutylenes, butyl rubber or styrene copolymers. This adhesive material further includes 3 to 60 percent by weight of material or synthetic polymers, which can for example be gluten and long chain polymers of methyl vinyl ether/maleic acid, capable of developing elastomeric properties when hydrated.

Useful in the cohesive layer 18 is the Doyle et al. adhesives such as those commercially available as Durahesive or DuoDerm CGF®. Nevertheless, while the above adhesives are well suited for use with the present invention, they are merely meant to be exemplary. Any appropriate adhesive as would be known to those in the art could be employed including skin compatible adhesives and fluid interactive adhesives.

The cohesive layer is preferably larger in size than the absorbent layer, and especially the same size as the porous, non-stick layer or film and the same size as the protective cover (all of which are described later below).

In one embodiment of the invention, the adhesive material of the wound dressing may further include an adjuvant such as an antimicrobial or wound healing agent. Other agents typically used in wound care may further be included. For example, between about 2 and 20 percent, and preferably about 10 percent, by weight of zinc oxide can be included in the adhesive material.

The protective cover backing film 20 of the wound dressing covers the cohesive layer described above. It is preferably a suitable polymeric material. It can be of any plastic, polymer film, nonwoven material, weave or the like, or combination thereof, known in the art. Suitable examples include polyester fibers, polypropylene fibers, nylon fibers, composite olefin fibers and cellulose fibers. Other polymeric backing films can be selected from the various materials commonly employed in ostomy and medical devices. For example, polyolefins such as polypropylene, ethylene acrylic acids, ethylene vinyl acetates, polyvinylchlorides, polyether sulfones, polyether ketones, polyether urethanes, polyurethanes, etc., can be used. The backing layer is preferably made of a thin, flexible, conformable, resilient, supple, limp or flimsy material that can flex or bend to conform to irregular surfaces or contours, such as those of anatomical body parts. The protective cover backing film 20 can be transparent to permit visualization, or it can be opaque. The protective cover backing film 20 can be air permeable to allow oxygen to penetrate the dressing, as well as moisture vapor permeable to allow moisture from the skin surface to escape through the dressing. Additionally, the protective cover backing film 20 can be liquid, air or bacteria impermeable as chosen by those in the art for a particular wound or surface to be treated. Polyurethane films are preferred, such as flexible polyurethane silicone coated polymers. Embossed polyethylene films also may be used.

The absorbent layer including an absorbing means or wound pad 14 can also be of any convenient material or materials used as wound dressings in the wound care art. Typical materials include, but are not limited to, natural and synthetic polymeric absorbents, hydrocolloid/polysaccharide absorbents, cellulosic absorbents, gum and resin absorbents, inorganic absorbents, gel-forming fluid-interactive adhesive dressings, wool, cotton, lint and superabsorbents, i.e., water swellable polymers typically in the form of fiber or flock material. The structure of the absorbing means or wound pad may comprise a complete laminated dressing, e.g., that described by Pawelchak et al. in U.S. Pat. No. 4,538,603 wherein an occlusive dressing commercially available from ConvaTec known as Duo-Derm™ is disclosed. Pawelchak et al. describe dressings comprising an adhesive layer of semi-open cell polymeric foam and/or a polymeric film backing layer. The dressing may also include a second adhesive layer to enhance cohesion. Similarly, U.S. Pat. No. 4,793,337 describes a dressing like the double adhesive structure of Pawelchak et al., but which also includes a layer of calcium alginate wool or fiber interposed the adhesive layer. Additionally, the absorbing means can be the same material as the adhesive in cohesive layer 18 when appropriate as known to those in the art.

These or any other pad, gauze or wound film known in the art, e.g., materials from the diaper and incontinence arts, can also be utilized as the absorbing means or wound pad. Specific suitable dressings include Sunbeam Process absorbent materials (Gelman Technology), the Composite Air Laid Superabsorbent Pad (Dry Forming Processes) and Polysteen Superabsorbent Fiber Flock SAFF (Hanfspinnerei Steen & Co.). Most preferred for the absorbing means or wound pad 14 is a fibrous matrix of absorbent and/or superabsorbent materials. A cellulose matrix containing a superabsorbent, e.g., carboxymethylcellulose, can be used. Sodium polyarcrylate is especially preferred, and particular in granular or powder form. One suitable layer contains Salsorb® (superabsorbent) in an air laid fiber matrix marketed by Gelok International Laminate. Such a superabsorbent can comprise about 30% by weight of the absorbing means or wound pad 14. "Superabsorbents" are water insoluble materials which are capable of absorbing and retaining large amounts of water or other aqueous fluid in comparison to their own weight. Disposable goods manufactured using superabsorbents can be more comfortable, less bulky, and longer lasting than similar products made with traditional absorbents such as cellulose fibers. Unlike a sponge, liquid binds to the superabsorbent even under pressure (for example when a wound is in a position such that a patient may have occasion to sit on the dressing).

Regardless of the material chosen, the absorbent layer including an absorbing means or wound pad 14 should be capable of handling the wound fluids so as to protect the wound and surrounding areas from the deleterious effects thereof. This can be accomplished by, for example, the ability of the absorbing means or wound pad to remove or "wick" the fluids away from the wounds.

As mentioned above, the absorbing means or wound pad 14 can also be a gauze or a composite pad. Under these circumstances, the absorbing means or wound pad may further include an overwrap, e.g., a polyester nonwoven overwrap (e.g., those available from Kendall, Fasson, Semex and the like) and a non-adherent facing as is known in the art.

Especially preferred is a sodium polyacrylate superabsorbent powder sandwiched between two layers of cellulose tissue.

The porous, non-stick layer or film overlying a wound-facing surface of the absorbent layer 22 is shown in some of the figures. This layer is more specifically a nonwoven or apertured film. The non-stick layer does not, itself, normally contain hydrocolloids, but rather the present dressing relies upon hydrocolloids which may be contained in the absorbent layer when a hydrocolloid environment is desired. In another embodiment, this layer can be, for example, made of cellulose pulp (e.g., 85 grams per square meter) and polyolefin fibers (22 grams per square meter) and covered by a non-woven cover layer (20 grams per square meter) on its top and bottom. The non-woven cover layer may be an air-laid, wet-laid or spun-laid rayon, polyester or preferably polypropylene. Such a pad is available in its assembled state from Cellosoft Co. of Sweden and is sold as catalogue #202.150. Alternatively, a pad having a pattern of holes formed through the pad and comprising a combination of polypropylene and tissue can be used. The pad includes a non-woven polypropylene cover on top and bottom and is available from IFC Non Woven, Inc. of Jackson, Fla. Still another layer may be, for example, 5 ply bonded polypropylene. Each polypropylene layer may be sonically welded without the use of binders. A Delnet can be used. Especially preferred is a polypropylene non-woven.

While the cohesive layer 18 generally holds the components of the dressing together, the porous, non-stick layer or film preferably is not connected to the absorbent layer. It is believed that this may provide increased flexibility of the dressing.

Figure 2:
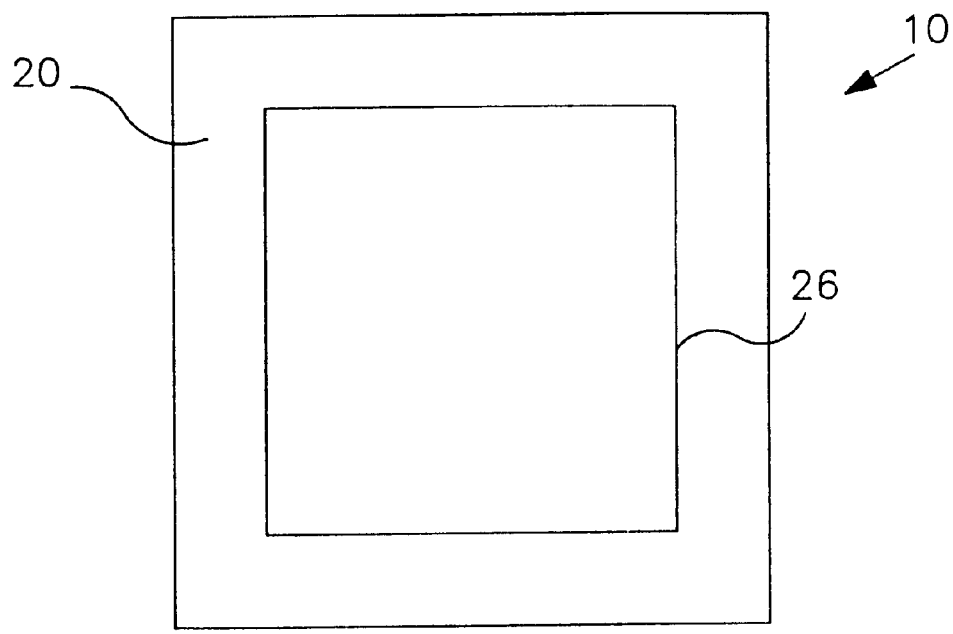
FIG. 2 is a top view of one embodiment of the present invention.
Figure 3:
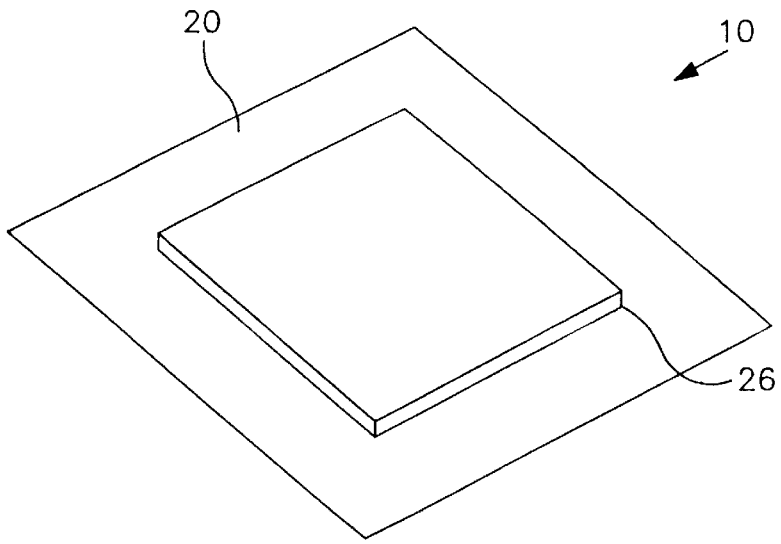
FIG. 3 is a perspective view of one embodiment of the present invention.

FIGS. 2 and 3 represent a top view and a perspective view, respectively, of an embodiment of a wound dressing in accordance with the instant invention. Wound dressing 10 is shown. The outer limits 26 of the wound pad are also indicated, as is top film 20. The wound dressing 10 and the absorbent layer including an absorbing means or wound pad 14 can be of any convenient size and shape depending on the wound to be dressed. They are depicted as concentric squares merely for simplicity.

Figure 4:
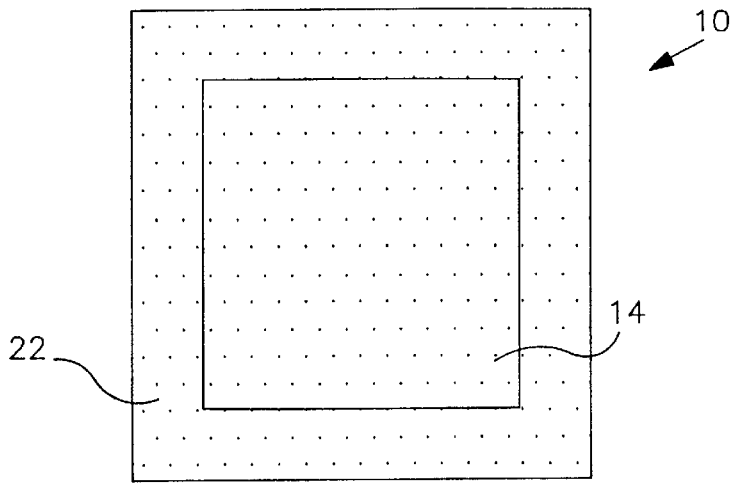
FIG. 4 is a bottom view of one embodiment of the present invention.

FIG. 4 represents a bottom view of an embodiment of a wound dressing 10 of the instant invention. Also shown is the non-stick layer or film 22 which overlays the wound facing surface of the absorbing means or wound pad 14.

All of the components of the dressing can be of any suitable thickness as would be known to those in the art. For example, the cohesive layer 18 can be of any suitable thickness. This thickness may be about 5 to 60 mils, or about 5 to 20 mils, or about 10 to 16 mils, or even about 8 to 12 mils. The most preferred thickness is about 1 mil. The protective film is preferably 0.5 to 3 mils thick, more preferably about 1 mil thick. The absorbent layer and non-stick layer or film can both also be of any suitable thickness such as $\frac{1}{16}$ inch each.

The nonadherent dressing of this invention avoids the use of an adhesive in direct contact with the wound or surrounding skin. It is further "non-adherent" in nature in that the non-stick materials utilized at the skin contact layer substantially eliminates adherence of the dressing to the wound site. When the protective layer is occlusive or semi-occlusive, a moist wound environment can be maintained if desired. When a hydrocolloid-containing material is used in the absorbent layer, a beneficial hydrocolloid environment is provided without the gel-like skin-contacting adhesive mass of prior art hydrocolloid dressings.

Thus, an excellent wound healing envirouient is provided while maximizing protection to the wound and surrounding skin. Dressing changes are greatly facilitated by the present nonadherent product in that damage to the wound is virtually eliminated. Further, using the present invention, more frequent dressing changes can take place without the need for a two-piece baseplate-type system as disclosed by Frank et al., U.S. Pat. No. 4,909,243.

The dressings of the invention can be held in place by any convenient means. For example, they can be held in place with tape or preferably with a wrap.

Methods of wound treatment using the present dressings and a tape or wrap, preferably providing a desired compression, are also integral parts of the present invention.

It will be appreciated by those of ordinary skill in the art that the embodiments shown can be modified without departing from the spirit and scope of the invention.

What is claimed is:

1. A non-adherent wound dressing comprising
   (a.) sodium polyacrylate superabsorbent powder sandwiched between two layers of cellulose tissue;
   (b.) a polypropylene non-woven larger in size than said sodium polyacrylate superabsorbent powder sandwiched between two layers of cellulose tissue, and overlying a wound-facing surface of said sodium polyacrylate superabsorbent powder sandwiched between two layers of cellulose tissue, such that a portion of said polypropylene non-woven extends beyond the length and width of said sodium polyacrylate superabsorbent powder sandwiched between two layers of cellulose tissue;
   (c.) a polyurethane film which is larger in size than said sodium polyacrylate superabsorbent powder sandwiched between two layers of cellulose tissue, but generally no greater in size than said polypropylene non-woven; and
   (d.) a cohesive layer of a hydrocolloid adhesive generally being substantially the size and shape of the polyurethane film which is adhered to its non-wound-facing surface and having said sodium polyacrylate superabsorbent powder sandwiched between two layers of cellulose tissue and the extending portion of said polypropylene non-woven adhered to its wound facing surface.

2. A method of treating a wound comprising applying to a woud site a non-adherent dressing, wherein the non-adherent dressing comprises
   (a.) sodium polyacrylate superabsorbent powder sandwiched between two layers of cellulose tissue;
   (b.) a polypropylene non-woven larger in size than said sodium polyacrylate superabsorbent powder sandwiched between two layers of cellulose tissue, and overlying a wound-facing surface of said sodium polyacrylate superabsorbent powder sandwiched between two layers of cellulose tissue, such that a portion of said polypropylene non-woven extends beyond the length and width of said sodium polyacrylate superabsorbent powder sandwiched between two layers of cellulose tissue;
   (c.) a polyurethane film which is larger in size tlan said sodium polyacrylate superabsorbent powder sandwiched between two layers of cellulose tissue, but generally no greater in size the said polypropylene non-woven; and
   (d.) a cohesive layer of a lhydrocolloid adhesive generally being substantially the size and shape of the polyurethane film which is adhered to its non-wound-facing surface and having said sodium polyacrylte superabsorbent powder sandwiched between two layers of cellulose tissue and the extending portion of said polypropylene non-woven adhered to its wound facing surface.

3. The method of claim 2 further comprising securing said non-adherent dressing to said wound site with a wrap.

4. A system for treating a wound comprising
   (i.) a non-adherent wound dressing comprising
      (a.) sodium polyacrylate superabsorbent powder sandwiched between two layers of cellulose tissue;
      (b.) a polypropylene non-woven larger in size tlian said sodium polyacrylate superabsorbent powder sandwiched between two layers of cellulose tissue, and overlying a wound-facing surface of said sodium polyacrylate superabsorbent powder sandwiched between two layers of cellulose tissue, such that a portion of said polypropylene non-woven extends beyond the length and width of said sodium polyacrylate superabsorbent powder sandwiched between two layers of cellulose tissue;
      (c.) a polyurethane film which is larger in size than said sodium polyacrylate superabsorbent powder sandwiched between two layers of cellulose tissue, but generally no greater in size than said polypropylene non-woven; and
      (d.) a cohesive layer of a hydrocolloid adhesive generally being substantially the size and shape of the polyurethane film which is adhered to its non-wound-facing surface and having said sodium polyacrylate superabsorbent powder sandwiched between two layers of cellulose tissue and the extending portion of said polypropylene non-woven adhered to its wound facing surface; and
   (ii.) a wrap for securing said non-adherent dressing to a wound site.

* * * * *